(12) United States Patent
Heng et al.

(10) Patent No.: US 8,907,312 B2
(45) Date of Patent: Dec. 9, 2014

(54) CYTOMETRY SYSTEM WITH SOLID NUMERICAL-APERTURE-INCREASING LENS

(75) Inventors: Xin Heng, Emeryville, CA (US); Paul Patt, Lafayette, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 321 days.

(21) Appl. No.: 13/212,459

(22) Filed: Aug. 18, 2011

(65) Prior Publication Data

US 2012/0211679 A1    Aug. 23, 2012

Related U.S. Application Data

(60) Provisional application No. 61/375,578, filed on Aug. 20, 2010.

(51) Int. Cl.
*G01N 15/06* (2006.01)
*H01J 3/14* (2006.01)
*G01N 15/14* (2006.01)
*G01N 21/64* (2006.01)

(52) U.S. Cl.
CPC .......... *G01N 15/1434* (2013.01); *G01N 15/147* (2013.01); *G01N 2021/6421* (2013.01); *G01N 21/645* (2013.01)
USPC .......................................... 250/573; 250/216

(58) Field of Classification Search
CPC ................................ G01N 21/85; G01N 21/64
USPC ................ 250/573–577, 483.1, 484.2, 484.3, 250/484.4, 486.1, 487.1, 216; 359/250–253, 272, 296, 665; 348/749; 356/124, 246, 410, 411, 417, 436
See application file for complete search history.

(56) References Cited

U.S. PATENT DOCUMENTS 4,074,939 A  *  2/1978 Rabl ............................. 356/435
5,521,699 A      5/1996 Kosaka et al.
(Continued)

FOREIGN PATENT DOCUMENTS

JP      61-173141      8/1986
JP      62-108855      6/1987
(Continued)

OTHER PUBLICATIONS

Ghislain, L., et al., "Near-field scanning solid immersion microscope," Applied Physics Letters, 1998, vol. 72, No. 22, pp. 2779-2781.

(Continued)

*Primary Examiner* — Georgia Y Epps
*Assistant Examiner* — Don Williams
(74) *Attorney, Agent, or Firm* — Kilpatrick Townsend & Stockton LLP

(57) ABSTRACT

A flow cytometry system includes a flow element through which a cell is transported in a flowing fluid. The flow element includes a bore bounded by a wall. A light source is configured to illuminate the cell. An optical system receives light emanating from the cell and directs at least some of the received light to a light sensor. The optical system includes a numerical-aperture-increasing lens at a wall of the flow element. At least some of the received light passes through the numerical-aperture-increasing lens. The flow cytometry system may also include a beam splitter that directs two wavelength bands of the emanating light such that light in two wavelength band preferentially reach different sensing locations via different paths. The system may also include an optical element placed in one of the paths, shifting a focal location of the affected path to compensate for chromatic aberration of the numerical-aperture-increasing lens.

31 Claims, 5 Drawing Sheets

(56) References Cited

U.S. PATENT DOCUMENTS

| | | | |
|---|---|---|---|
| 5,939,709 | A | 8/1999 | Ghislain et al. |
| 5,973,842 | A | 10/1999 | Spangenberg |
| 6,373,792 | B1 | 4/2002 | Belser et al. |
| 6,376,821 | B1 | 4/2002 | Kikuchi et al. |
| 6,633,439 | B1 | 10/2003 | Xu et al. |
| 6,687,058 | B1 | 2/2004 | Ippolito et al. |
| 7,038,856 | B2 | 5/2006 | Quake et al. |
| 7,116,407 | B2 | 10/2006 | Hansen et al. |
| 7,468,789 | B2 * | 12/2008 | Czarnek ............. 356/246 |
| 2002/0097658 | A1 | 7/2002 | Worthington et al. |
| 2004/0085644 | A1 | 5/2004 | Patton et al. |
| 2004/0260157 | A1 | 12/2004 | Montes |
| 2009/0257057 | A1 | 10/2009 | Novotny et al. |
| 2010/0090127 | A1 | 4/2010 | Yekta et al. |

FOREIGN PATENT DOCUMENTS

| | | |
|---|---|---|
| JP | 03-235037 | 10/1991 |
| JP | 07-043307 | 2/1995 |
| JP | 2002-503097 | 1/2002 |
| JP | 2002-310886 | 10/2002 |
| JP | 2006-105881 | 4/2006 |
| JP | 2006-234663 | 7/2006 |
| JP | 2008-536099 | 9/2008 |
| WO | WO 2005/033654 A2 | 4/2005 |
| WO | 2007/074929 | 7/2007 |

OTHER PUBLICATIONS

International Search Report and Written Opinion of PCT/US2011/048496 mailed on Dec. 22, 2011, 10 pages.

Ippolito, S., et al., "High spatial resolution subsurface microscopy," Applied Physics Letters, 2001, vol. 78, No. 26, pp. 4071-4073.

Terris, B., et al, "Near-field optical data storage," Applied Physics Letters, 1996, vol. 68, No. 2, pp. 141-143.

Vamivakas, A., et al., "A case study for optics: The solid immersion microscope," American Journal of Physics, 2008, vol. 76, No. 8, pp. 758-768.

Wu, Q., et al., "Realization of numerical aperture 2.0 using a gallium phosphide solid immersion lens," Applied Physics Letters, 1999, vol. 75, No. 26, pp. 4064-4066.

Office action of related Japanese Application No. 2013523388 mailed on Feb. 26, 2014, 8 pages. English translation included.

Office action in related Japanese Application No. 2013-523388, issued on Aug. 26, 2014, 4 pages. English translation included.

* cited by examiner

CYTOMETRY SYSTEM WITH SOLID NUMERICAL-APERTURE-INCREASING LENS

This application claims the benefit of U.S. Provisional Patent Application No. 61/375,578 filed Aug. 20, 2010 and titled "Cytometry System with Solid Numerical-aperture-increasing Lens", the entire disclosure of which is hereby incorporated by reference herein.

BACKGROUND OF THE INVENTION

Cytometry is a technical specialty concerned with the counting and characterization of biological cells. FIG. 1 shows a simplified diagram of a system for performing a technique known as imaging flow cytometry. In a basic form of imaging flow cytometry, cells 101 are suspended in a fluid and entrained single-file in a narrow transparent tube 102. The entrainment can be accomplished by any of several methods, including hydrodynamic focusing. A light source 103 illuminates each cell 101 as it passes a measurement location. Light source 103 may be, for example, a laser. Light from light source 103 is scattered by the cell 101 being measured. Some light 105 is gathered by an objective lens 106 and redirected to form an image at a light sensor 107. Light sensor 107 may be, for example, a component of a microscope or camera. Various optical components may cooperate with objective lens 106 in directing light 105 to sensor 107, including, for example, partially reflective mirror 108 and an additional lens 109. Output signals from sensor 107 are sent to a processing unit 110, which may store and analyze the signals to discern information about each cell, for example its size and some information about its internal structure.

BRIEF SUMMARY OF THE INVENTION

In some embodiments, a flow cytometry system comprises a flow element through which a cell is transported in a flowing fluid. The flow element comprises a bore bounded by a wall, and at least a portion of the wall is substantially transparent. The flow cytometry system also comprises a light source configured to illuminate the cell, a light sensor, and an optical system that receives light emanating from the illuminated cell and directs at least some of the received light to the light sensor. The optical system comprises a numerical-aperture-increasing lens at the wall of the flow element, and at least some of the received light passes through the numerical-aperture-increasing lens. In some embodiments, the numerical-aperture-increasing lens is a solid numerical-aperture-increasing lens. The optical system may receive and direct light emanating by reflection from the cell. The optical system may receive and direct light emanating by fluorescence from the cell. The numerical-aperture-increasing lens may be integrally formed with the wall of the flow element. The light sensor may comprise an electronic light sensor. The light sensor may comprise a linear electronic light sensor. The flow cytometry system may perform cross section imaging of the cell. The light source may comprise a laser.

In some embodiments, the light sensor comprises a first light sensing location, and the flow cytometry system further comprises a beam splitter that directs two wavelength bands of the emanating light such that light in one wavelength band preferentially reaches the first light sensing location via a first path, and that light in the other wavelength band preferentially reaches a second light sensing location via a second path. The first and second light sensing locations may be coplanar. The first and second light sensing locations may comprise separate locations on the light sensor. In some embodiments, the flow cytometry system comprises an optical element placed in either the first or second path, the optical element configured to compensate for chromatic aberration of the numerical-aperture-increasing lens by shifting a focal location of one of the paths. The optical element may be a transmissive flat plate. The optical element may be a lens.

In other embodiments, a flow element for flow cytometry comprises a wall defining a bore through the flow element, at least a portion of the wall being substantially transparent, and a numerical-aperture-increasing lens at the wall. The numerical-aperture-increasing lens may be integrally formed with the wall. The bore may be substantially cylindrical. The bore may comprise at least one substantially flat side. The numerical-aperture-increasing lens may comprise a semi-spherical protrusion from the wall. The numerical-aperture-increasing lens may be configured such that an inner surface of the flow element substantially corresponds with an aplanatic surface of the numerical-aperture-increasing lens.

In other embodiments, a method of performing flow cytometry comprises providing a flow element, the flow element comprising a bore bounded by a wall, transporting a cell through the flow element, illuminating the cell using a light source, and receiving, using an optical system, light emanating from the illuminated cell, the optical system including a numerical-aperture-increasing lens at the wall of the flow element, and the received light passing through the numerical-aperture-increasing lens. In these embodiments, the method further comprises directing the received light to a light sensor. In some embodiments, the method further comprises receiving, at a processing unit, signals from the light sensor representing an intensity of light falling on the light sensor. The method may further comprise interpreting the signals to discern information about the cell. The method may further comprise providing a beam splitter that splits the received light into at least two wavelength bands, the light in the two wavelengths bands preferentially reaching different sensing locations via different paths. The method may further comprise inserting an optical element into one of the paths to shift a focal location of the path, to compensate for chromatic aberration introduced by the numerical-aperture-increasing lens.

According to other embodiments, a system for performing cytometry includes a mechanism that generates relative motion between a cell and a sensing location, a light source configured to illuminate the cell, a light sensor, and an optical system that receives light emanating from the illuminated cell and directs at least some of the received light to the light sensor. The optical system further includes a numerical-aperture-increasing lens, and at least some of the received light passes through the numerical-aperture-increasing lens. In some embodiments, the mechanism that generates relative motion between the cell and the scanning location includes a flow element through which the cell moves, the cell suspended in a flowing fluid. In some embodiments, the mechanism that generates relative motion between the cell and the scanning location includes a plate that carries the cell. The plate may include a disk. The system may further include a coupling liquid between the numerical-aperture-increasing lens and the plate.

DETAILED DESCRIPTION OF THE INVENTION

In research applications, it is desirable that a cytometry system produce images of very high resolution and magnification. For example, a researcher studying virus trafficking in cell cytoplasm may need to image extremely small biological objects. The resolution of a microscope or other imaging device is fundamentally limited by the diffraction or Rayleigh limit, related to the numerical aperture (NA) of the objective lens and the wavelength of light being gathered by the lens. Accordingly, a very high NA is desirable, in order to achieve high resolution.

In some applications, more than one light wavelength is of interest. For example, in fluorescence cytometry, cell structures may be tagged with fluorophores that emanate light by fluorescence upon excitation by a light source. Different fluorophores may emanate light in different wavelength ranges, and an imaging objective lens should accordingly be corrected for chromatic aberration, so that detailed images may be collected simultaneously in more than one light wavelength.

These imaging requirements for magnification, resolution, and chromatic correction may have traditionally necessitated a sophisticated and expensive objective lens having a very short working distance. For example, a front surface of the objective lens may need to be within 1 millimeter or less of the subject being studied. This limited working distance is especially troublesome in flow cytometry, in which the structure required for cell handling may not readily fit within the working distance of the objective lens.

A lens with a longer working distance may be used, but at the expense of resolution, as a longer working distance may necessitate a smaller NA. Without sufficient resolution, a cytometry system may not be able to recognize sub-cellular structures.

Figure 1:
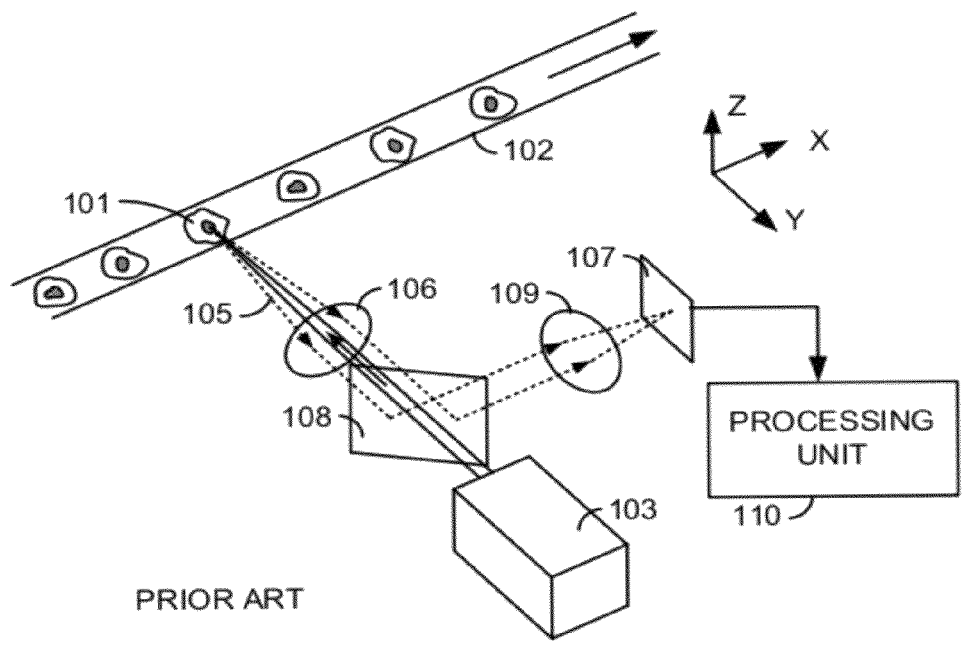
FIG. 1 shows a simplified diagram of a system for performing a technique known as imaging flow cytometry.
Figure 2:
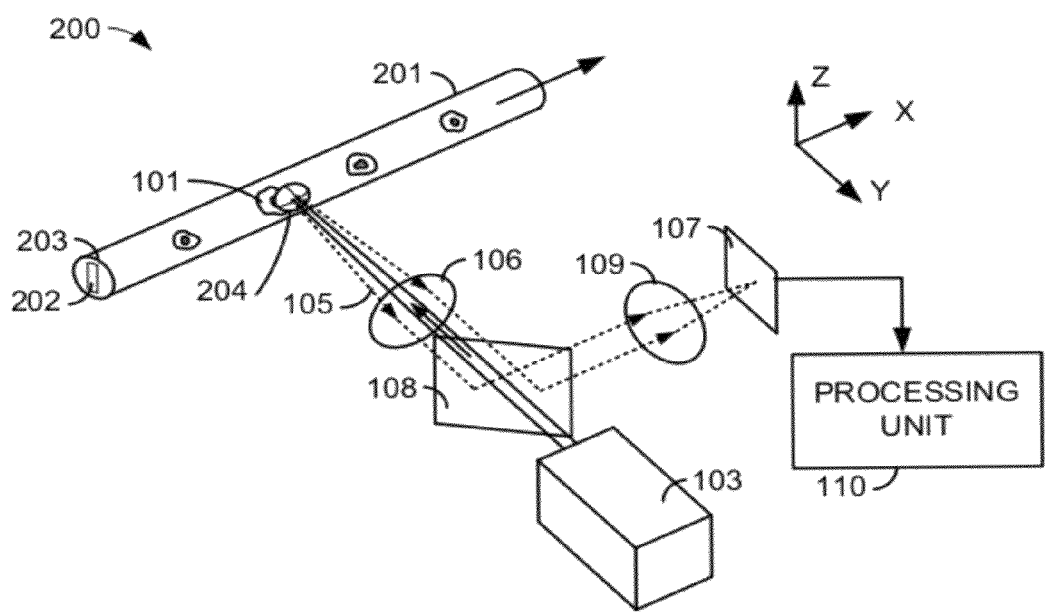
FIG. 2 illustrates a cytometry system in accordance with one embodiment of the invention.

FIG. 2 illustrates a cytometry system 200 in accordance with one embodiment of the invention. Cytometry system 200 includes a flow element 201, through which cells 101 are transported in a flowing fluid. At least a portion of flow element 201 is substantially transparent, so that illumination light can reach cells 101, and so that light emanating from cells 201 can be detected outside flow element 201. Example flow element 201 comprises a bore 202 bounded by a wall 203. In example flow element 201, bore 202 comprises flat sides, but other shapes are possible. For example, bore 202 may be substantially cylindrical. Cytometry system 200 also includes a numerical-aperture-increasing lens, in this example a solid numerical-aperture-increasing lens (SNAIL) 204. SNAIL 204 is a semi-spherical protrusion integrally formed with wall 203, for example by molding. SNAIL 204 may also be formed separately from flow element 201 and affixed to wall 203, or otherwise placed in position at the wall of flow element 201.

Cytometry system 200 illuminates cells 101 and captures light emanating from cells 101 from the same direction. Light from light source 103 passes through partially reflective mirror 108, objective lens 106, and SNAIL 104 to reach cells 101. Light emanating from cells 101 passes through SNAIL 104 and objective lens 106, and is substantially redirected by mirror 108 toward second lens 109 and light sensor 107. Mirror 108 may be also filter the light. For example, if cytometry system 200 is intended image cells in light wavelengths emitted from the cells by fluorescence, mirror 108 may preferentially reflect light emanated by fluorescence while preferentially passing light reflected from the cells. One of skill in the art will recognize that other arrangements are possible within the scope of the appended claims. For example, light source 103 may be positioned to illuminate cells 101 from a different direction, not aligned with the optical axis of objective lens 106.

The function of SNAIL 204 is to effectively increase the NA of the system including objective lens 106, thereby enabling use of an objective lens with a longer working distance than would otherwise be feasible while still providing very high resolution imaging.

Figure 3:
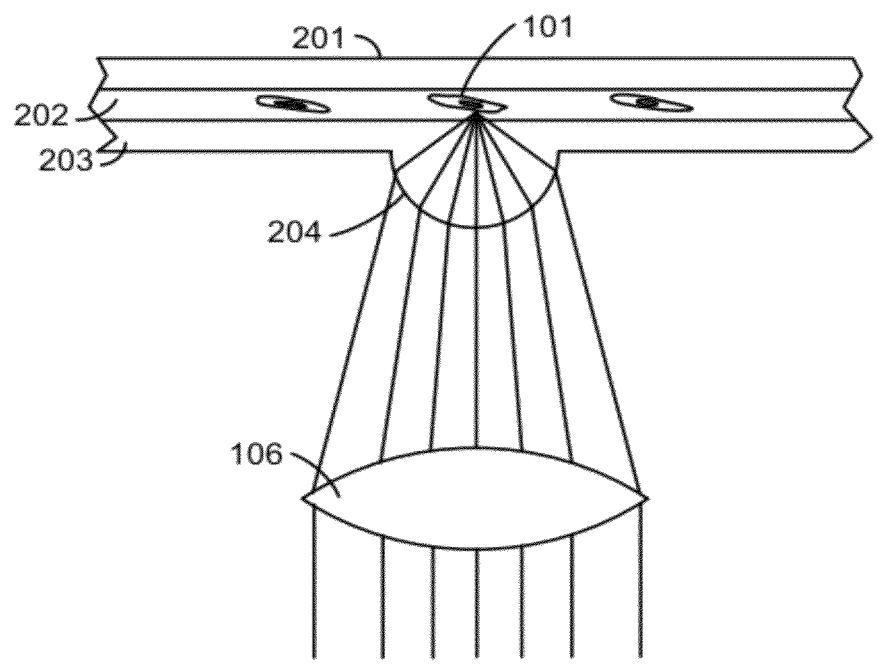
FIG. 3 illustrates a partial section view of the cytometry system of FIG. 2.

FIG. 3 illustrates a partial section view of cytometry system 200, as seen from the Z direction shown in FIG. 2, and positioned so that objective lens 106 is at the bottom of the view and flow element 201 is at the top. FIG. 3 illustrates the function of SNAIL 204. SNAIL 204 is an example of a solid immersion lens (SIL). The NA, and therefore also the achievable resolution, of an optical system can be effectively increased by immersing the object to be studied in a medium having a higher refractive index than the medium in which the rest of the optical system operates. In FIG. 3, objective lens 106 is in air having a refractive index of essentially 1.0. Flow element 201 and SNAIL 204 may be made of a material or materials having a higher refractive index, for example BK7 glass with a nominal refractive index of about 1.518, or polycarbonate with a nominal refractive index of about 1.584, or SF11 glass with a nominal refractive index of about 1.785. (As will be discussed in more detail below, due to the dispersion inherent in optical materials, the actual refractive index a material is wavelength dependent.) While it is preferable that SNAIL 204 and wall 203 of flow element 201 be matched in refractive index, this is not a necessity. In flow cytometry, cells 101 are also immersed in a medium having a refractive index higher than that of air, for example water having a nominal refractive index of about 1.333. Other liquid media may be used. While it is preferable that the liquid medium and wall 203 of flow element 201 be relatively closely matched in refractive index, this is also not a necessity.

As can be seen in FIG. 3, SNAIL 204 enables a much larger cone of light emanating from cell 101 to be captured by objective lens 106 than would be the case if cell 101 were immersed in air. In fact, a SIL having a refractive index n can increase the NA of an optical system by as much as a factor of $n^2$. For example, if SNAIL 204 is made of SF11 glass with a refractive index n of 1.785 and objective lens 106 operates at an NA of 0.3, then the effective NA of the system may be as high as $(1.785)^2*0.3=0.95$, which may be higher than even a very high quality, high magnification objective lens operating without the benefit of a SNAIL.

Figure 4:
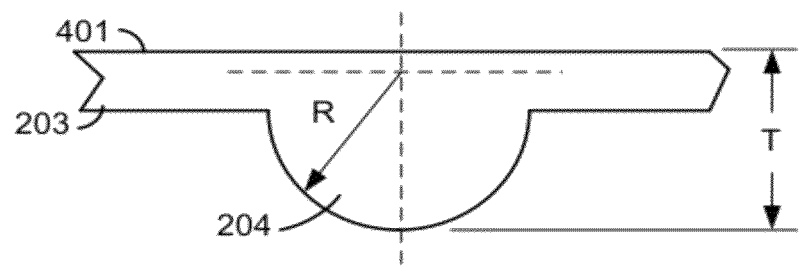
FIG. 4 illustrates one example arrangement for a numerical-aperture-increasing lens.

Preferably, the dimensions of SNAIL 204 are selected to such that SNAIL 204 does not introduce excessive aberration into the optical system. FIG. 4 illustrates one example arrangement for a SNAIL 204 that is semi-spherical, having a surface radius R. The distance T indicates the distance from the apex of SNAIL 204 to inner surface 401 of wall 203. If distance T is selected such that T=R(1+1/n), where n is the refractive index of SNAIL 204 and wall 203, then inner surface 401 corresponds to the so-called aplanatic surface of SNAIL 204, and SNAIL 204 introduces very little if any geometric aberration for imaging objects such as cells 101 that are essentially at surface 401 and near the optical axis of the system. While SNAIL 204 is illustrated in FIG. 4 as being semi-spherical, aspheric shapes may alternatively be used.

Figure 5A:
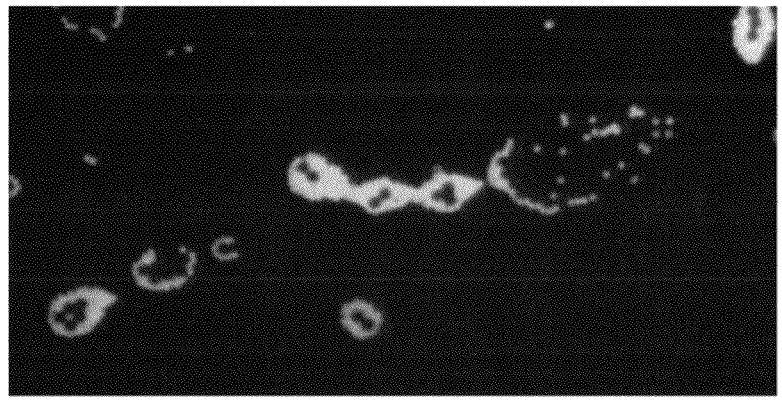
FIGS. 5A and 5B illustrate actual images of clusters of fluorescent beads having a diameter of 2.5 µm, taken without and with the benefit of a numerical-aperture-increasing lens.
Figure 5B:
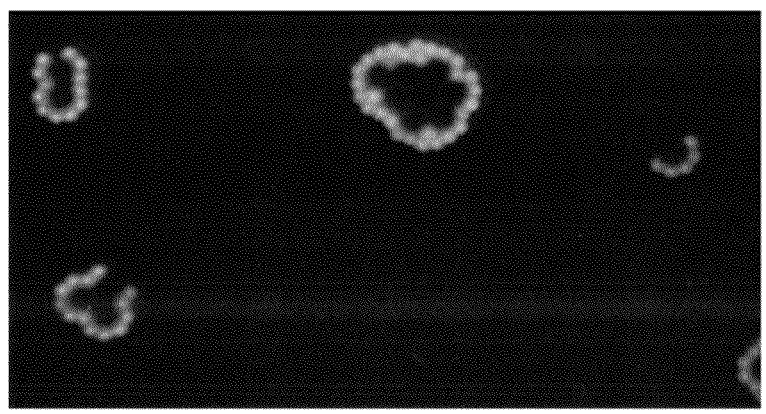

The benefits of including SNAIL 204 in the system are significant. For example, without the use of SNAIL 204, a 60× objective may be required to achieve satisfactory system resolution, but the 60× objective may not have adequate working distance for flow cytometry. The introduction of SNAIL 204 may enable the use of a 10× objective with a much longer working distance, at a fraction of the cost of the 60× objective. The increased NA not only improves the system resolution, but also results in the capture of more photons from the test sample than in a system with lower NA, which can be a significant advantage for fluorescence cytometry and other low-light applications. Additionally, the magnification of the system is increased, also by a factor of about $n^2$. FIGS. 5A and 5B illustrate actual images of clusters of fluorescent beads having a diameter of 2.5 μm each. Both images were taken using a 10× objective lens having a nominal NA of 0.3. FIG. 5A was taken without the benefit of a SNAIL, while the system used to take the image of FIG. 5B included a SNAIL. The increases in both magnification and resolution are readily apparent.

Referring again to FIG. 2, light sensor 107 may be any kind of light sensor suitable for a particular application. For example, light sensor 107 may be an electronic light sensor comprising an array of photosensitive sites referred to as pixels, and may produce electrical signals representing the intensity of light falling on the pixels, from which a digital image of a cell may be produced. Light sensor 107 may comprise a two-dimensional array of pixels, a linear array of pixels, multiple linear arrays of pixels, or only a single photosensitive detector.

A optical system utilizing a SNAIL such as SNAIL 204 may be especially suited to line-scan or cross section cytometry systems such as those described in provisional U.S. patent applications 61/162,072 filed Mar. 20, 2009 and titled "Line-Scan Camera Based Multi-color Fluorescent Imaging and Imaging Flow Cytometry", 61/232,113 filed Aug. 7, 2009 and titled "Serial-Line-Scan Encoded Multi-color Fluorescence Microscopy and Imaging Flow Cytometry", and 61/235,608 filed Aug. 20, 2009 and titled "High-Speed Cellular Cross Sectional Imaging", the entire disclosures of which are hereby incorporated by reference herein for all purposes. Line-scan and cross section imaging techniques may use a smaller field of view than systems employing two-dimensional sensors. For example, a full imaging cytometry system may have a field of view 200 μm×200 μm. While many different kinds and sizes of cells may be studied by a system such as cytometry system 200, a typical cell may be about 10 μm across. Line-scan and cross section imaging techniques may image a cell only when it is near the center of the field of view, for example within an area of about 50 μm×50 μm centered on the system optical axis. As such, any aberrations introduced by SNAIL 204 or by any refractive index mismatches between SNAIL 204, wall 203 of flow element 201, and the liquid in which the cells are suspended may be especially tolerably small.

While geometrical aberrations introduced by SNAIL 204 may be made acceptably small, SNAIL 204 may also introduce chromatic aberration into the optical system. Because the refractive index of any optical material is inherently wavelength dependent, light of different wavelengths will not necessarily be focused at the same location by a particular optical system. This wavelength dependent effect on image quality is called chromatic aberration. Sophisticated lenses are designed to reduce chromatic aberration using multiple optical elements of differing materials (having differing dispersion characteristics) and selected powers to at least partially counter the effects of chromatic aberration. For example, lenses 106 and 109 shown in FIG. 2 may be chromatically corrected. The introduction of SNAIL 204, a simple monolithic element, may re-introduce some chromatic aberration into the system. For applications in which multiple color imaging is to be performed, this chromatic aberration may significantly reduce the ability of the system to obtain sufficient resolution in all of the colors of interest unless some other form of correction is applied.

Multi-color imaging may be especially useful in applications that detect light emanating from the cells of interest by fluorescence. For example, different cells or cell features in a test sample may be tagged by different fluorophore markers. The different markers may be excited by the same or different sources, but emit light by fluorescence in different wavelength ranges. The markers may be, for example, Cy3 and Cy5 cyanine dyes. Cy3 is excited maximally at 550 nm and emits maximally at 570 nm. Cy5 is excited maximally at 649 nm and emits maximally at 670 nm.

One approach to imaging a test sample with multiple wavelength ranges of interest is to image the different colors on different cameras, each camera adjusted to properly focus its respective color range.

Figure 6:
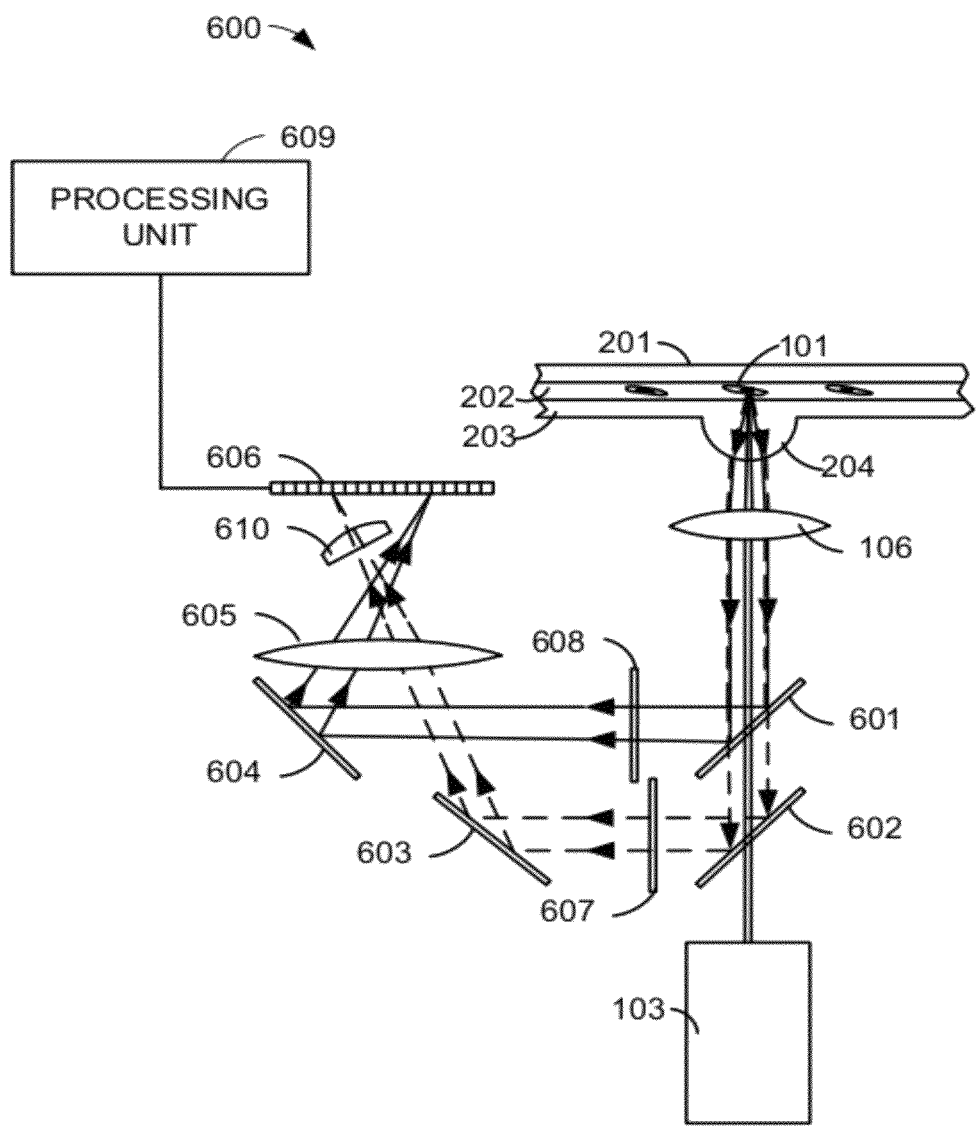
FIG. 6 illustrates a cytometry system in accordance with another embodiment of the invention.

FIG. 6 illustrates a cytometry system 600 in accordance with another embodiment of the invention. In example cytometry system 600, light source 103 illuminates cell 101 being transported through flow element 201. Light source 103 may be a laser or another kind of light source. As depicted, light source 103 directs a beam through objective lens 106, through SNAIL 204, and to cell 101. The beam may pass through other elements as well, or any other suitable illumination arrangement may be used. As a result of illumination by light source 103, light emanates from cell 101, for example by reflection, fluorescence, or both. Light containing multiple wavelength ranges may emanate, indicated in FIG. 6 by solid and broken lines. For example, if light source 103 is a broadband source, then broadband light may reflect from cell 101. Even if light source 103 is a narrow band or essentially monochromatic source such as a laser, multiple light colors may emanate from cell 101 by fluorescence of different kinds of fluorescent markers.

The emanating light is redirected by SNAIL 204 and collected by objective lens 106, to be eventually refocused by second lens 605 onto light sensor 606. Objective lens 106 and second lens 605 may be comprised in an infinity-corrected optical system, allowing for the insertion of various other optical components between them. Light sensor 606 may be an electronic light sensor comprising an array of photosensitive sites referred to as pixels, and may produce electrical signals representing the intensity of light falling on the pixel. The signals are passed to a processing unit 609, which may produce a digital image a cell. Light sensor 606 may comprise a two-dimensional array of pixels, a linear array of pixels, multiple linear arrays of pixels, or discrete photosensitive sites. Light sensor 606 may be, for example, a complementary metal oxide semiconductor (CMOS) sensor, a charge coupled device (CCD) sensor, one or more photomultiplier tubes (PMT), or another kind of sensor.

An arrangement of mirrors and filters makes up an exemplary beam splitter that directs two wavelength bands of the emanating light such that light in one wavelength band preferentially reaches a first light sensing location via a first path, and that light in the other wavelength band preferentially reaches a second light sensing location via a second path. For example, mirror 601 may be a dichroic mirror configured to preferentially reflect light in a particular wavelength band (depicted in solid lines in FIG. 6) and to preferentially transmit light not in the particular wavelength band. Mirror 602 may be a simple partially reflective mirror, or may also have filter characteristics, but in any event substantially reflects light in the second wavelength band (depicted in broken lines). The light emanating from cell 101 is thus split, with some wavelengths mainly following one path and other wavelengths mainly following a different path.

Optional additional filters 607 and 608 may further condition the spectral content of the light following the two different paths, for example to reduce crosstalk between the two sensing channels. Mirrors 603 and 604 may direct the light through second lens 605 to light sensor 606. In the example shown in FIG. 6, the two light paths reach different sensing locations on the same light sensor 606. Signals generated by light sensor 606 will then represent two images, formed in light of different colors and shifted spatially by the beamsplitter comprising mirrors 601 and 602. Alternatively, the different sensing locations may be on different sensors provided to receive the two different images.

Because light sensor 606 is substantially planar, and because of chromatic aberration in the system, the two images may not both focus at light sensor 606 without some form of correction. In system 600, the correction is provided by inserting an additional optical element 611 in one of the paths. The optical element 610 is configured to compensate for chromatic aberration of SNAIL 204 by shifting a focal location of light in one of the wavelength bands. As shown in FIG. 6, optical element 610 is a positive lens inserted into the path having the longest focal distance, so that the affected path is shortened. Other kinds of optical elements may be used. For example, optical element 610 could be a simple flat transmissive plate, or a negative lens could be placed into the other optical path to lengthen it.

Figure 7:
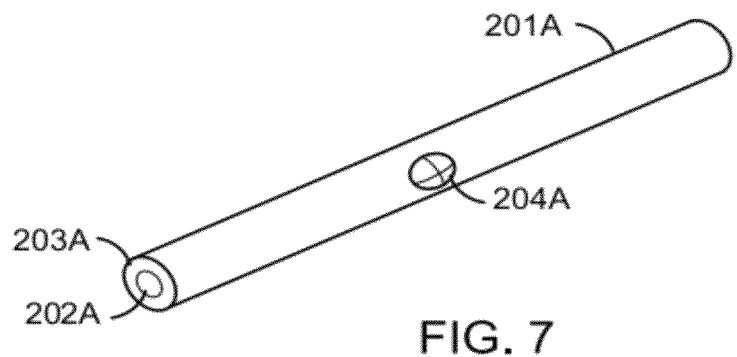
FIG. 7 illustrates a flow element in accordance with another embodiment.

FIG. 7 illustrates and alternative embodiment for flow element 201. In this embodiment, flow element 201A has a generally cylindrical bore 202A bounded by a wall 203A. A flow element suitable for use in embodiments of the invention may be formed in any of a number ways. Merely by way of example, a flow element such as flow element 201 or 201A could be molded as an integrated unit from a clear material such as a glass or polymer, including SNAIL 204 or 204A. Alternatively, the wall and bore of the flow element could be formed by extrusion, and the SNAIL formed separately and attached later using an adhesive. Preferably, the adhesive would be index matched to the wall and SNAIL being joined. These or other fabrication methods may result in a low-cost device that may be an interchangeable or even disposable component of a flow cytometry system. A flow element such as element 201 or 201A may also include features for facilitating connection to other parts of a flow cytometry system, for example mounting surfaces or lugs, bolt holes, hose connectors, or other features.

Figure 8:
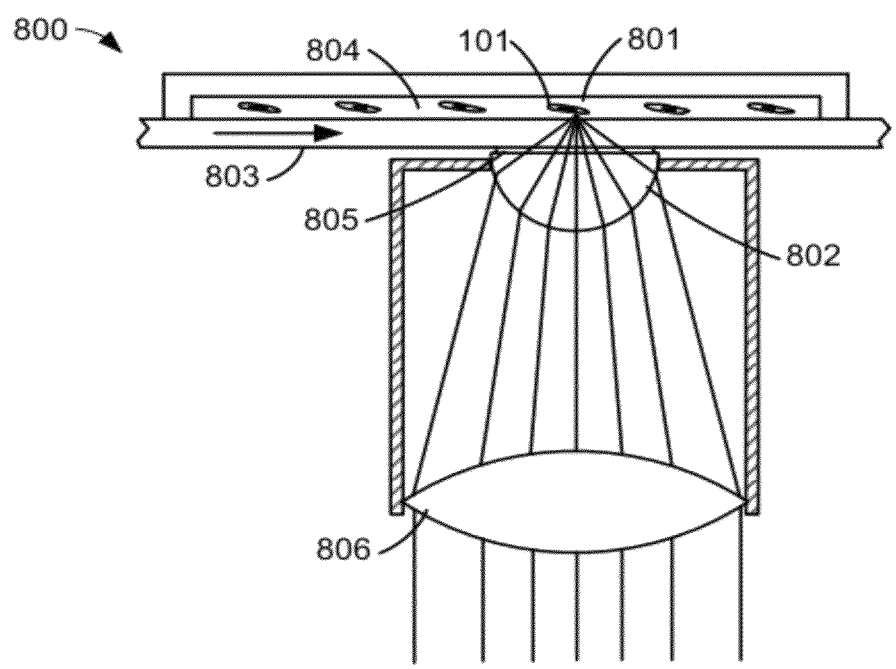
FIG. 8 illustrates a portion of a system for performing cytometry, in accordance with other embodiments of the invention.

FIG. 8 illustrates a portion of a system 800 for performing cytometry, in accordance with other embodiments of the invention. System 800 comprises a mechanism that generates relative motion between a cell 101 and a sensing location 801. Sensing location 801 may be, for example, near a focal point of an objective lens such as lens 806, operating in concert with a SNAIL 802. Preferably, objective lens 806 and SNAIL 802 are held in fixed relationship. A light source and light sensor (not shown) illuminate cell 101 and receive light emanating from cell 101. Cell 101 and other cells may be adhered to or otherwise carried by a plate 803. Plate 803 may be, for example, a microscope slide or a disk. The relative motion between cell 101 and sensing location 801 may be generated by moving plate 803, by moving objective lens 806 and SNAIL 802, or by moving both at different velocities. In one embodiment, objective lens 806 and SNAIL 802 are held stationary, while plate 803 in the form of a rotating disk is moved. In another example arrangement, lens 806 and SNAIL 802 may move radially in relation to a rotating disk on which cell 101 and other cells are adhered or otherwise carried.

Cell 101 may be suspended in a fluid, for example in a fluid chamber 804. Preferably, a coupling liquid 805 also resides between SNAIL 802 and plate 803 to maintain the immersion of cell 101 in a high-index environment. Ideally, the refractive indices of the materials involved in the immersion are matched, for example, the material of which plate 803 and SNAIL 802 are made, the fluid in which cell 101 is suspended, if any, and coupling liquid 805. However, in practice perfect index matching is not generally needed to achieve benefits.

While system 800 is shown with SNAIL 802 and objective lens 103 below plate 803, the system could also be inverted, so that SNAIL 802 and objective lens 103 are above plate 803. Other arrangements may be possible as well. A system according to embodiments of the invention may utilized a lower cost objective lens 806 than would otherwise be needed to achieve comparable image quality without SNAIL 802, and may also have relaxed requirements for axial registration and focus adjustment.

While embodiments of the invention have been illustrated as scanning cells confined in a linear tube or carried by a plate, one of skill in the art will recognize that embodiments of the invention may be utilized in systems using any of a wide range of cell delivery techniques, including electrophoresis, pressure driven flow, optical tweezers, motorized translation stage, and others. Cells may be conveyed as a payload in an oil emulsion, in an electrowetting-actuated droplet, or via magnetic transport assisted by magnetic bead tagging. It is intended that the claims not be limited by the cell delivery method utilized.

In the claims appended hereto, the term "a" or "an" is intended to mean "one or more." The term "comprise" and variations thereof such as "comprises" and " comprising," when preceding the recitation of a step or an element, are intended to mean that the addition of further steps or elements is optional and not excluded. The invention has now been described in detail for the purposes of clarity and understanding. However, those skilled in the art will appreciate that certain changes and modifications may be practiced within the scope of the appended claims.

What is claimed is:

1. A flow cytometry system, comprising:
    a flow element through which a cell is transported in a flowing fluid, the flow element comprising a bore bounded by a wall, at least a portion of the wall being substantially transparent;
    a light source configured to illuminate the cell;
    a light sensor; and
    an optical system that receives light emanating from the illuminated cell and directs at least some of the received light to the light sensor, the optical system comprising an objective lens and a numerical-aperture-increasing lens, the numerical-aperture-increasing lens being at the wall of the flow element, at least some of the received light passing through the numerical-aperture-increasing lens before reaching the objective lens, wherein the numerical-aperture-increasing lens effectively increases the numerical aperture of the optical system as compared with the numerical aperture of the objective lens without the numerical-aperture-increasing lens.

2. The flow cytometry system of claim 1, wherein the numerical-aperture-increasing lens is a solid numerical-aperture-increasing lens.

3. The flow cytometry system of claim 1, wherein the optical system receives and directs light emanating by reflection from the cell.

4. The flow cytometry system of claim 1, wherein the optical system receives and directs light emanating by fluorescence from the cell.

5. The flow cytometry system of claim 1, wherein the numerical-aperture-increasing lens is integrally formed with the wall of the flow element.

6. The flow cytometry system of claim 1, wherein the light sensor comprises an electronic light sensor.

7. The flow cytometry system of claim 1, wherein the light sensor comprises a linear electronic light sensor.

8. The flow cytometry system of claim 1, wherein the flow cytometry system performs cross section imaging of the cell.

9. The flow cytometry system of claim 1, wherein the light source comprises a laser.

10. The flow cytometry system of claim 1, wherein the light sensor comprises a first light sensing location, the flow cytometry system further comprising:
a beam splitter that directs two wavelength bands of the emanating light such that light in one wavelength band preferentially reaches the first light sensing location via a first path, and that light in the other wavelength band preferentially reaches a second light sensing location via a second path.

11. The flow cytometry system of claim 10, wherein the first and second light sensing locations are coplanar.

12. The flow cytometry system of claim 10, wherein the first and second light sensing locations comprise separate locations on the light sensor.

13. The flow cytometry system of claim 10, further comprising:
an optical element placed in either the first or second path, the optical element configured to compensate for chromatic aberration of the numerical-aperture-increasing lens by shifting a focal location of one of the paths.

14. The flow cytometry system of claim 13, wherein the optical element is a transmissive flat plate.

15. The flow cytometry system of claim 13, wherein the optical element is a lens.

16. A flow element for flow cytometry, the flow element comprising:
a wall defining a bore through the flow element, at least a portion of the wall being substantially transparent; and
a numerical-aperture-increasing lens directly coupled to the wall, the numerical-aperture-increasing lens configured to receive and at least partially converge light emanating from within the bore such that the numerical-aperture-increasing lens increases the numerical aperture of an optical system including an objective lens used to image cells within the bore.

17. The flow element of claim 16, wherein the numerical-aperture-increasing lens is integrally formed with the wall.

18. The flow element of claim 16, wherein the bore is substantially cylindrical.

19. The flow element of claim 16, wherein the bore comprises at least one substantially flat side.

20. The flow element of claim 16, wherein the numerical-aperture-increasing lens comprises a semi-spherical protrusion from the wall.

21. The flow element of claim 16, wherein the numerical-aperture-increasing lens is configured such that an inner surface of the flow element substantially corresponds with an aplanatic surface of the numerical-aperture-increasing lens.

22. A method of performing flow cytometry, the method comprising:
providing a flow element, the flow element comprising a bore bounded by a wall;
transporting a cell through the flow element;
illuminating the cell using a light source;
receiving, using an optical system, light emanating from the illuminated cell, the optical system including an objective lens and a numerical-aperture-increasing lens, the numerical-aperture-increasing lens being at the wall of the flow element, the received light passing through the numerical-aperture-increasing lens before reaching the objective lens, wherein the numerical-aperture-increasing lens effectively increases the numerical aperture of the optical system as compared with the numerical aperture of the objective lens without the numerical-aperture-increasing lens; and
directing the received light to a light sensor.

23. The method of claim 22, further comprising receiving, at a processing unit, signals from the light sensor representing an intensity of light falling on the light sensor.

24. The method of claim 23, further comprising interpreting the signals to discern information about the cell.

25. The method of claim 22, further comprising providing a beam splitter that splits the received light into at least two wavelength bands, the light in the two wavelengths bands preferentially reaching different sensing locations via different paths.

26. The method of claim 25, further comprising inserting an optical element into one of the paths to shift a focal location of the path, to compensate for chromatic aberration introduced by the numerical-aperture-increasing lens.

27. A system for performing cytometry, the system comprising:
a mechanism that generates relative motion between a cell and a sensing location;
a light source configured to illuminate the cell;
a light sensor; and
an optical system that receives light emanating from the illuminated cell and directs at least some of the received light to the light sensor, the optical system comprising an objective lens and a numerical-aperture-increasing lens, the numerical-aperture-increasing lens being at the wall of the flow element, at least some of the received light passing through the numerical-aperture-increasing lens before reaching the objective lens, wherein the numerical-aperture-increasing lens effectively increases the numerical aperture of the optical system as compared with the numerical aperture of the objective lens without the numerical-aperture-increasing lens.

28. The system of claim 27, wherein the mechanism that generates relative motion between the cell and the scanning location comprises a flow element through which the cell moves, the cell suspended in a flowing fluid.

29. The system of claim 27, wherein the mechanism that generates relative motion between the cell and the scanning location comprises a plate that carries the cell.

30. The system of claim 29, wherein the plate comprises a disk.

31. The system of claim 29, wherein the system further comprises a coupling liquid between the numerical-aperture-increasing lens and the plate.

* * * * *